United States Patent
Drakulic (10) Patent No.: US 7,395,109 B2
(45) Date of Patent: Jul. 1, 2008

(54) SYSTEM FOR, AND METHOD OF, MONITORING HEARTBEATS OF A PATIENT

(75) Inventor: Budimir Drakulic, Los Angeles, CA (US)

(73) Assignee: Signalife, Inc., Studio City, CA (US)

(*) Notice: Subject to any disclaimer, the term of this patent is extended or adjusted under 35 U.S.C. 154(b) by 83 days.

(21) Appl. No.: 11/008,706

(22) Filed: Dec. 9, 2004

(65) Prior Publication Data

US 2006/0129052 A1    Jun. 15, 2006

(51) Int. Cl.
  *A61B 5/0402*  (2006.01)
(52) U.S. Cl. ............... 600/509; 600/508; 600/519; 705/2; 705/3; 128/920; 128/923; 128/924
(58) Field of Classification Search ......... 600/508–509, 600/519; 705/2–3; 128/920, 923–924, 9
  See application file for complete search history.

(56) References Cited

U.S. PATENT DOCUMENTS

| | | | |
|---|---|---|---|
| 4,200,109 A | 4/1980 | McMorrow, Jr. | |
| 4,204,546 A | 5/1980 | Smith et al. | |
| 4,263,561 A | 4/1981 | Weber | |
| 4,608,987 A | 9/1986 | Mills | |
| 4,610,259 A | 9/1986 | Cohen et al. | |
| 4,679,568 A | 7/1987 | Blau et al. | |
| 4,803,996 A | 2/1989 | Peel et al. | |
| 4,838,275 A * | 6/1989 | Lee | 600/483 |
| 4,924,875 A | 5/1990 | Chamoun | |
| 4,928,704 A | 5/1990 | Hardt | |
| 4,974,598 A * | 12/1990 | John | 600/509 |
| 4,991,580 A * | 2/1991 | Moore | 600/509 |
| 5,038,782 A | 8/1991 | Gevins et al. | |
| 5,263,487 A | 11/1993 | Sakamoto et al. | |
| 5,275,172 A | 1/1994 | Ives | |
| 5,368,041 A | 11/1994 | Shambroom | |
| 5,513,649 A | 5/1996 | Gevins et al. | |
| 5,678,559 A | 10/1997 | Drakulic | |
| 6,496,705 B1 | 12/2002 | Ng et al. | |
| 6,549,804 B1 | 4/2003 | Osorio et al. | |
| 6,597,942 B1 | 7/2003 | Yonce | |
| 6,681,003 B2 | 1/2004 | Linder et al. | |

(Continued)

FOREIGN PATENT DOCUMENTS

CA    2324713    10/2000

(Continued)

*Primary Examiner*—Carl H. Layno
*Assistant Examiner*—Deborah Malamud
(74) *Attorney, Agent, or Firm*—Fulwider Patton LLP (57) ABSTRACT

Heart monitor signals indicating a patient's heart characteristics are amplified without affecting the signal characteristics. The amplified heart monitor signals with atypical characteristics are transmitted to a pattern recognition platform which stores the patient's previously provided signals with atypical characteristics. The patient's present and previously provided signals with atypical characteristics are compared to select the previously provided signals with characteristics closest to those of the presently provided signals. Database signals identifying different types of heart problems in third parties and having characteristics closest to the patient's selected atypical signals are chosen. Dependent upon the severity of the patient's heart problems identified by the chosen database signals, the monitor transmits the chosen database signals to an individual one of the patient's doctor, the patient's hospital and an emergency care facility.

37 Claims, 6 Drawing Sheets

U.S. PATENT DOCUMENTS

| | | |
|---|---|---|
| 6,772,004 B2 | 8/2004 | Rudy |
| 6,823,209 B2 | 11/2004 | Olson et al. |
| 2003/0100923 A1* | 5/2003 | Bjorling et al. ............... 607/9 |
| 2004/0044292 A1* | 3/2004 | Yasushi et al. ............. 600/509 |
| 2004/0117212 A1* | 6/2004 | Kong et al. ................... 705/2 |
| 2006/0089592 A1* | 4/2006 | Kadhiresan et al. .......... 604/65 |

FOREIGN PATENT DOCUMENTS

| | | |
|---|---|---|
| EP | 0486399 | 5/1992 |
| EP | 1275342 A2 | 7/2001 |

* cited by examiner

SYSTEM FOR, AND METHOD OF, MONITORING HEARTBEATS OF A PATIENT

This invention relates to a heart monitor for indicating characteristics of a patient's heart. More particularly, the invention relates to heart monitors which identify the specific problems, if any, of a patient's heart.

BACKGROUND OF A PREFERRED EMBODIMENT OF THE INVENTION

Measurements are provided in a patient of the functioning of various organs in a patient's body. For example, measurements are made of the functioning of the patient's heart and the patient's brain. These measurements are generally made by applying an electrode or electrodes to the skin of the patient at the appropriate position or positions on the patient's body.

The measurements of the functioning of different organs in the patient's body involve the acquisition of signals in different frequency ranges. For example, measurements of the patient's heart occur in a range of DC to approximately two hundred and fifty hertz (250 Hz) and measurements of the patient's brain occur in a range of DC to approximately one hundred and fifty hertz (150 Hz).

The measurement of the functioning of different organs in the patient's body involves signals of miniscule amplitude. For example, the range of voltages produced at an electrode attached to the patient's skin for a measurement of the patient's heart is approximately one half of a millivolt (0.5 mV) to approximately four millivolts (4 mV). The range of the voltages produced at an electrode attached to the patient's skin for a measurement of the patient's brain is approximately five microvolts (5 µV) to approximately three hundred microvolts (300 µV).

When an electrode is attached to the patient's skin to measure the function of an organ such as the patient's heart or brain, the signal generated from the organ has to penetrate from the patient's organ through the body and the patient's skin to the electrode.

Monitors have been provided for many years to measure the characteristics of a patient's heart. The monitors in the other class are disposed on belts which are wrapped around the patient's waist and attached at their opposite ends by a buckle or clasp so as to be retained on the patient's body at the patient's waist. A cable connects electrodes on the patient's body to the monitor. This is called an "ambulatory monitor"

The patient then engages in the normal activities for a period of approximately twenty four (24) hours. After the recording session, the patient returns the monitor to the doctor's office. The signals required for the monitor are then analyzed, either by the doctor or by someone knowledgeable with respect to heart signals, to determine if the patient's heart presents any problems.

There are at least two (2) major problems with the ambulatory heart monitors now in use. One problem is that the ambulatory heart monitor does not faithfully record the patient's heartbeat signals. This results in part from ambulatory movements of the patient during the twenty four (24) hour recording period. When the patient moves during the recording period, artifacts and noise signals are produced which cloud the heartbeat signals. Furthermore, the heartbeat signal is not faithfully reproduced when it is amplified.

Another problem is that the signals cannot be analyzed until the ambulatory monitor is returned to the doctor at the end of the twenty four (24) hour recording period. This is undesirable. It would be better if the heartbeat signals produced by the patient during the recording period could be instantaneously analyzed by experts to identify the problems, if any, in the patient's heart while the problems are occurring. This would be especially critical if the patient was suffering a heart attack during the testing period. Furthermore, it would be better if the signals could be instantaneously analyzed to determine the existence of the patient's heart problems and to determine the severity, if any, of the patient's heart problems and the steps, if any, that should or could be immediately taken, based upon the analysis, to ameliorate the patient's heart problems.

BRIEF DESCRIPTION OF A PREFERRED EMBODIMENT OF THE INVENTION

A heart monitor acquires signals representing a patient's heart characteristics. The signals are amplified without affecting the original signal characteristics. The heartbeat signals with unusual characteristics are then transmitted to a processing station. The station also contains, in a pattern recognition platform, the patient's previously generated heartbeat signals. The station compares the signals with unusual characteristics and the patient's previously generated signals and selects the previously generated signals closest in characteristics to the signals with the unusual characteristics. A comparator then compares the selected signals and database signals indicating different types of heart problems in third parties and selects the database signals closest in characteristics to the selected signals previously generated by the patient. Dependent upon the patient's heart problem severity indicated by the characteristics of the selected database signals), the monitor transmits the selected database signals to (a) the patient's doctor, (b) the patient's hospital or (c) an emergency number (e.g. 911).

DETAILED DESCRIPTION OF A PREFERRED EMBODIMENT OF THE INVENTION

Figures 1, 2:
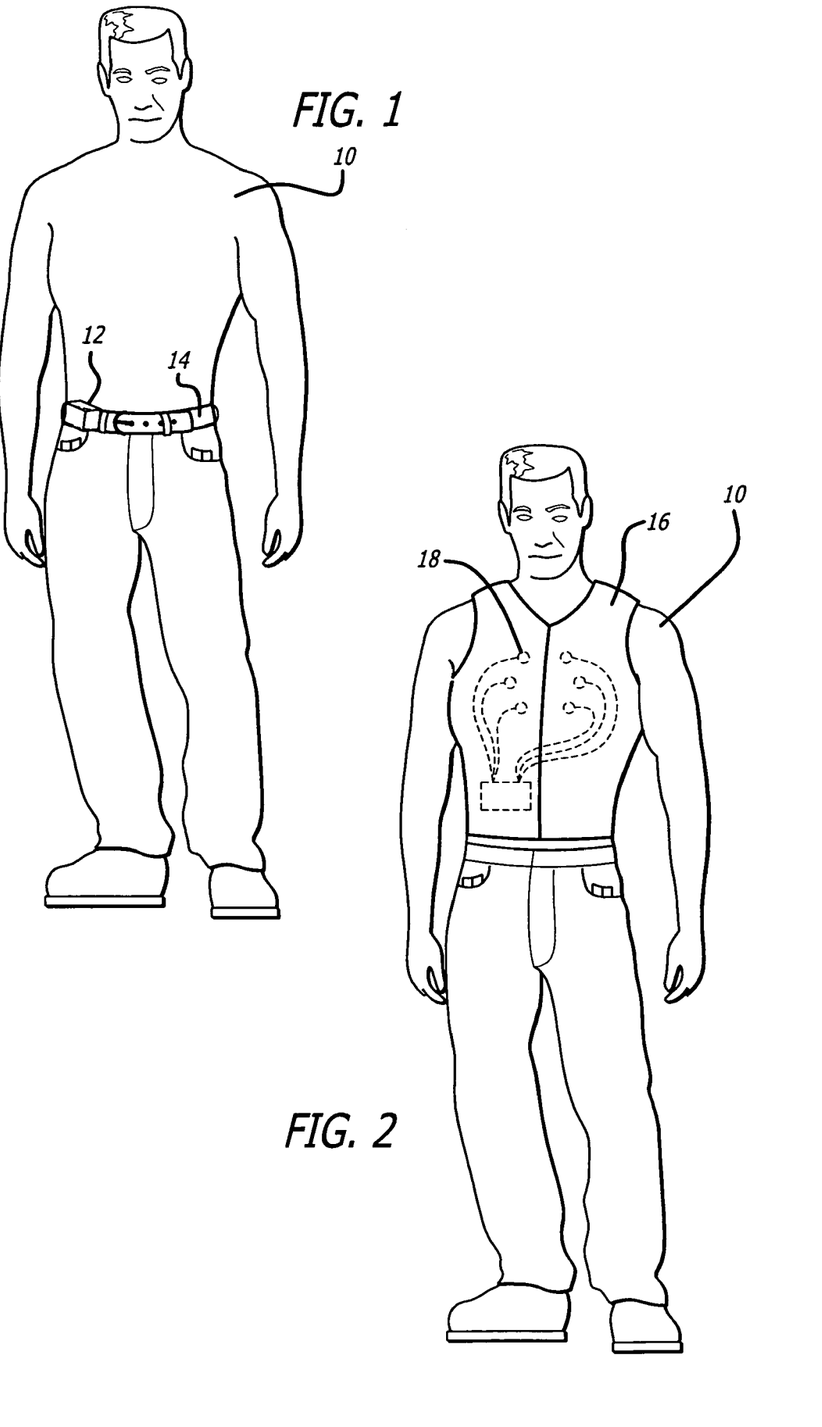
FIG. 1 is a schematic diagram of one embodiment of a system of the invention for monitoring heartbeats of a patient.
FIG. 2 is a schematic diagram of another embodiment of a system of the invention for monitoring heartbeats of a patient.

In a preferred embodiment of the invention, a patient 10 produces signals indicating heart characteristics of the patient. The signals may be recorded by a heart monitor 12 (FIG. 1) which is disposed on a belt 14 wrapped around the patient. An arrangement of a heart monitor disposed on a belt is well known in the art. The heart monitor may include electrodes attached to the patient's body at strategic positions on the patient's body to indicate the characteristics of the patient's heart at these strategic positions.

The signals may also be provided by a vest 16 (FIG. 2) which is worn by the patient and on which electrodes 18 are disposed for attachment to selected positions on the patient's body. An advanced embodiment of a vest 16 is disclosed and claimed in application Ser. No. 10/664,711 field in the USPTO on Sep. 17, 2003 in the name of Budimir S. Drakulic as a sole inventor and assigned of record to the assignee of record in this application.

The signals representing heart characteristics of the patient are amplified in an amplifier 20 (FIG. 3) which retains the characteristics of the signals produced by the patient's heart and does not produce noise. A suitable amplifier providing these advantages is disclosed and claimed in application Ser. No. 10/611,696 filed in the USPTO on Jul. 1, 2003 in the name of Budimir S. Drakulic as a sole inventor, and assigned of record to the assignee of record of this application. This amplifier will be disclosed in additional detail subsequently in this application since applicant wishes to include a recitation of this amplifier as an element in some of the claims.

Figure 3:
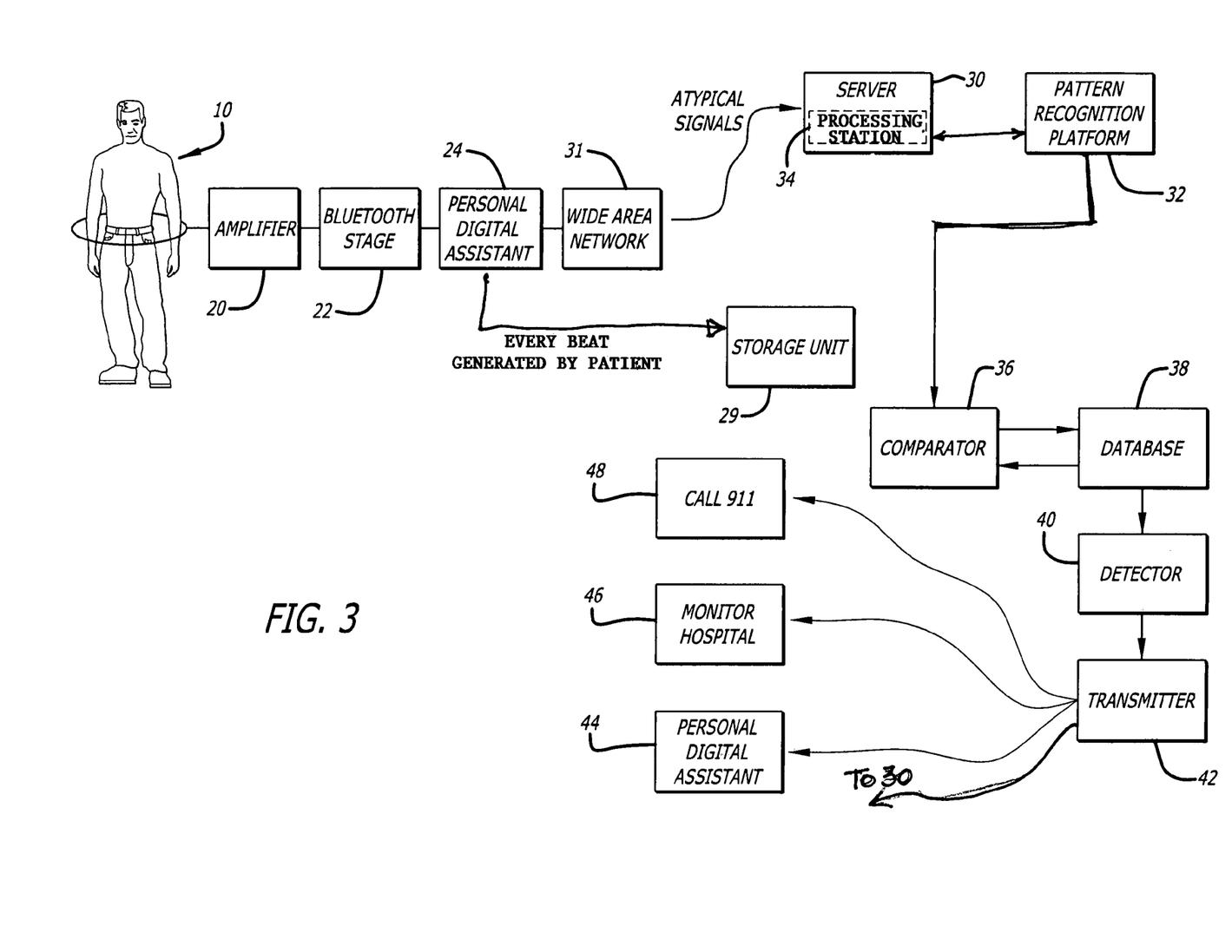
FIG. 3 is a schematic diagram in additional detail of a preferred system of the invention for monitoring heartbeats of a patient.

The signals from the amplifier 20 are transmitted by a Bluetooth stage 22 to a personal digital assistant (PDA) 24. Bluetooth stages are well known in the art to transmit signals through relatively short distances. PDAs are also well known in the art and may be considered to be a form of a pocket personal computer (PC).

Figure 4A:
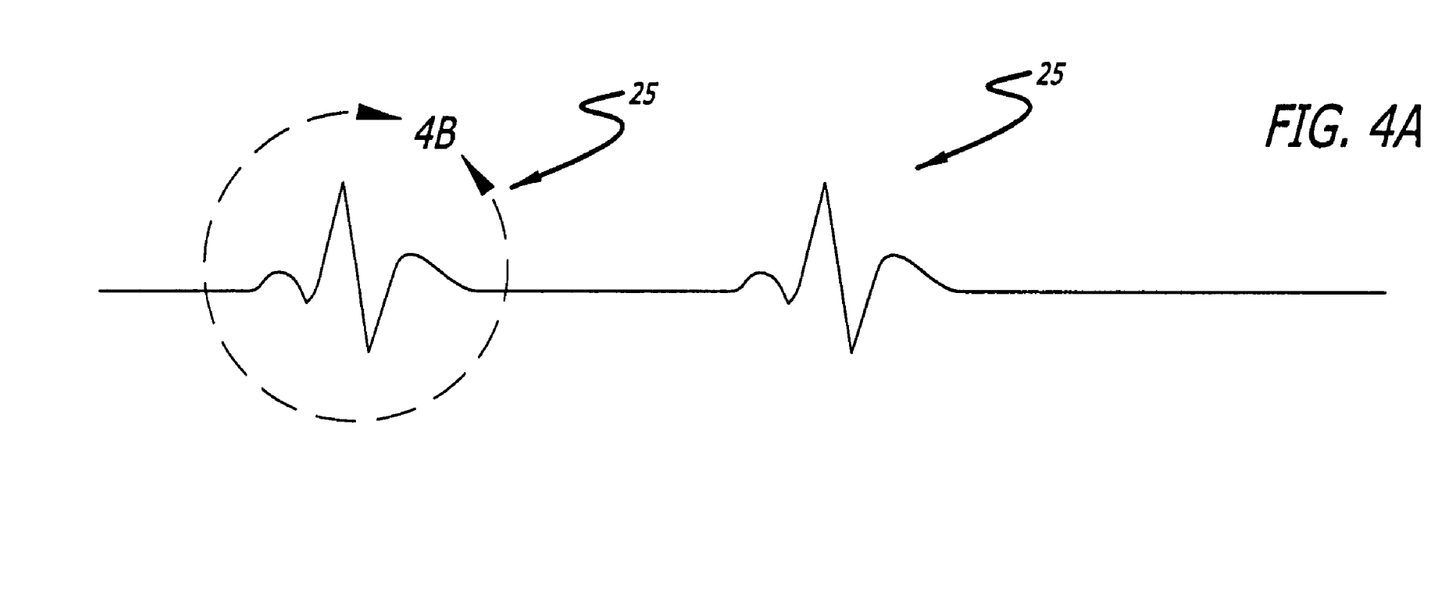
FIG. 4a is a schematic diagram illustrating the signals produced in each heartbeat of a patient.
Figure 4B:
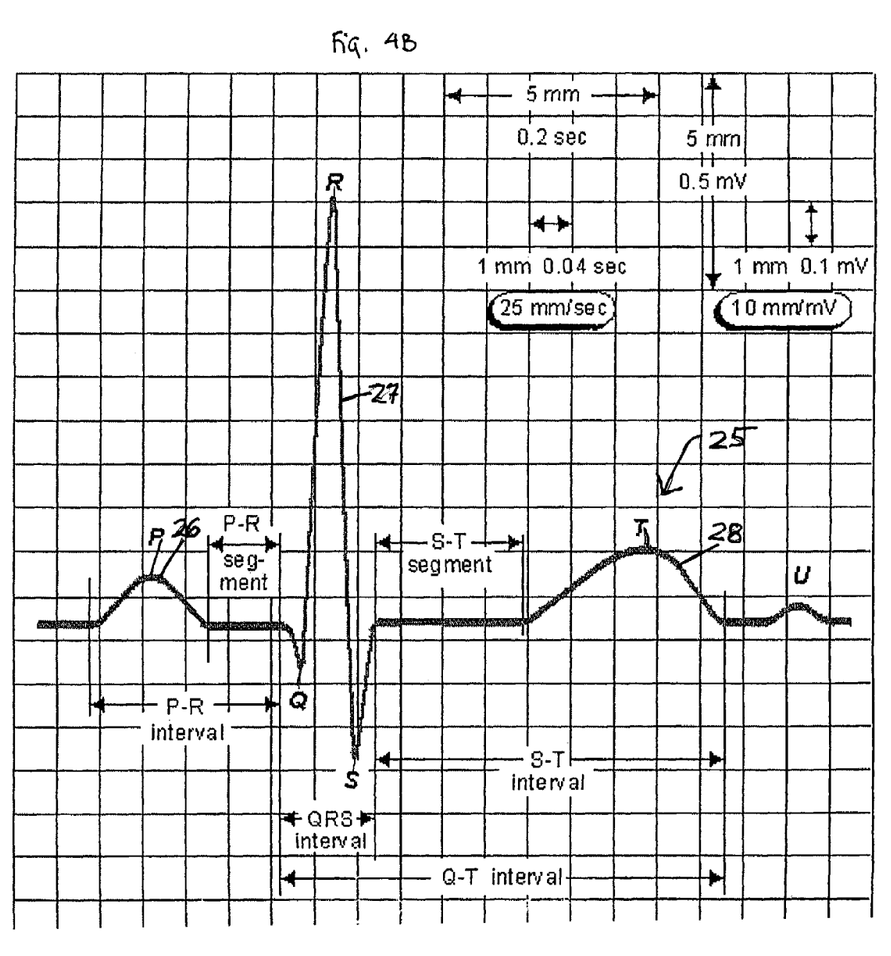
FIG. 4b is an enlarged schematic diagram illustrating one of the heartbeats of a patient.

A signal generally indicated at 25 in FIG. 4 is produced in each heartbeat of the patient 10. The signal 25 includes a first signal portion 26 having a positive portion rising to a positive peak P and a negative portion falling to a negative peak Q. The signal 25 also includes a second portion 27 having a positive portion rising to a positive peak R and a negative portion falling to a negative peak S. It additionally includes a third portion 28 having a positive portion rising to a positive peak T and then trailing downwardly, while still positive, from the positive peak T.

The durations of the portions 26, 27 and 28 of the patient's heart signals 25 are useful in determining whether there are any problems with the patient's heart and, if so, what these problems are. The peak amplitudes P, Q, R, S and T in each heartbeat signal are additionally useful in determining whether there are any problems with the patient's heart and, if so, what these problems are. The relative times of occurrence of the successive signal portions 26, 27 and 28 in each heartbeat also have some utility in determining whether there are any problems with the patient's heart and, if so, what these problems are.

The heartbeat signals 25 from the patient 10 are provided to a storage unit 29 to enable subsequent analysis if such an analysis should be desired. The atypical ones of the heartbeat signals are transmitted by a wide area network 31 (WAN) on a wireless basis to a server 30. Wide area networks are well known in the prior art. The atypical signals are those which are different from the signals which are typically generated by a patient. The server 30 is connected to a processing station 34.

The signal database in the processing station 30 contains signals which have been previously generated by the patient's heart when the patient's heart has been connected to the heart monitor 12. These signals may include signals which were generated when the patient was first connected to the heartbeat monitor. In addition, every time that the patient's heartbeat changes by more than a particular parameter, another sample of the patient's heartbeat is recorded in the processing station 34. In this way, a record is accumulated in the processing station 34 of progressive changes in the patient's heartbeat characteristics.

The processing station 34 selects the signals having characteristics which correspond most closely to the atypical signals transmitted to the server 30 through the wide area network 31. As previously indicated, the comparison is based upon various characteristics in the signals including the durations of the signal portions 26, 27 and 28, the wave shapes of the signal portions, the peak amplitudes P, Q, R, S and T of the signal portions and the relative times of occurrence of the signal portions 26, 27 and 28.

The signals selected by the processing station 34 are introduced to a pattern recognition platform 32 and then to a comparator 36 that also receives signals from a database 38. The database 38 stores signals generated by the patient and by third parties (other than the patient 10) and having characteristics indicating different types of heart problems. Each of the different signals in the database 38 provides heartbeat signals having characteristics which indicate an individual type of heart problem different from the heart problems indicated by the other signals in the database.

The comparator 36 compares the signals introduced to the comparator from the pattern recognition platform 32 and from the database 38 and selects, from the database, the signals having characteristics closest to the signals introduced to the comparator 36 from the pattern recognition platform. The comparison is made on the same basis as that discussed at paragraph 28.

A detector 40 is associated with the database 38. The detector 40 indicates where each of the signals selected from the database 38 is to be transmitted by a transmitter 42. If the signals selected from the database 38 indicate a heart problem, but not a serious heart problem, of the patient, the detector 40 instructs the transmitter 42 to transmit the selected database signals to the server 30. In this way, the patient's doctor can consult the server 30 and can analyze the signals and instruct the patient what to do to ameliorate any heart problems that the patient may have. Alternatively, the signals can be transmitted to a personal digital assistant (PDA) 44 of the patient's docket.

At the same time the patient's doctor is informed that an evaluation has to be made of the patient's atypical heartbeat. The doctors can access over the internet the patient's heartbeat in question, together with signals that are obtained from the database 38 and that are close in characteristics to the heartbeat signals obtained from a computer connected to the server 30. If the doctor is not in the office, the evaluation can be made by a personal digital assistant (PDA) 44 in a server client mode using the wireless internet.

When the selected database signals indicate heart problems in the patient of a moderate severity, the selected database signals may be transmitted to a monitor at a hospital 46. The signals may then be analyzed at the hospital 46 to determine the course of action that should be recommended to the patient 10. When the selected database signals are of real severity, the database signals may be transmitted on an urgency basis such as provided by the telephone number 911.

This is indicated at 48 in FIG. 3. While the patient is on the way to the hospital, the ambulance can access the server 30 and obtain all of the relevant data by connecting the ambulance computer over a wireless interface to the server 30.

Figure 7:
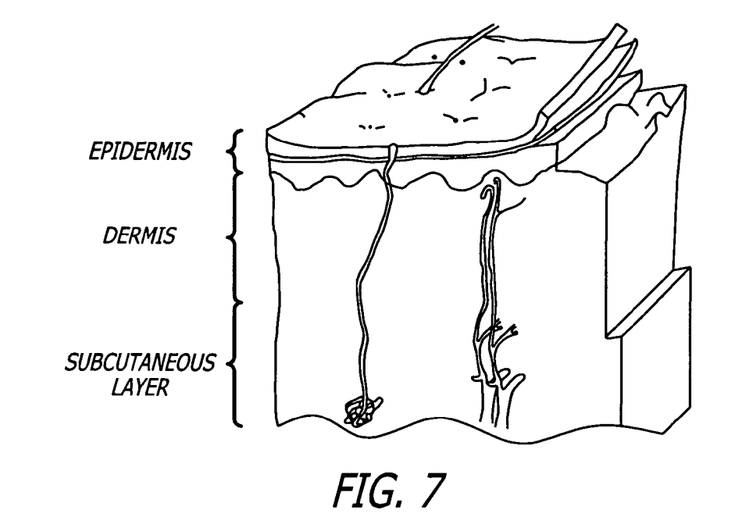
FIG. 7 is a schematic perspective view of the different layers in a patient's skin.

FIG. 7 is a schematic perspective view of the different layers in a patient's skin. As will be seen, there are a number of layers in the patient's skin. The bracketed indications on the left of FIG. 7 represent groupings of layers. These groupings of layers are respectively designated as epidermis, dermis and subcutaneous. They include layers designated as stratum corneum, barrier, stratum granulosum, stratum germinativum and papillae.

Figure 8:
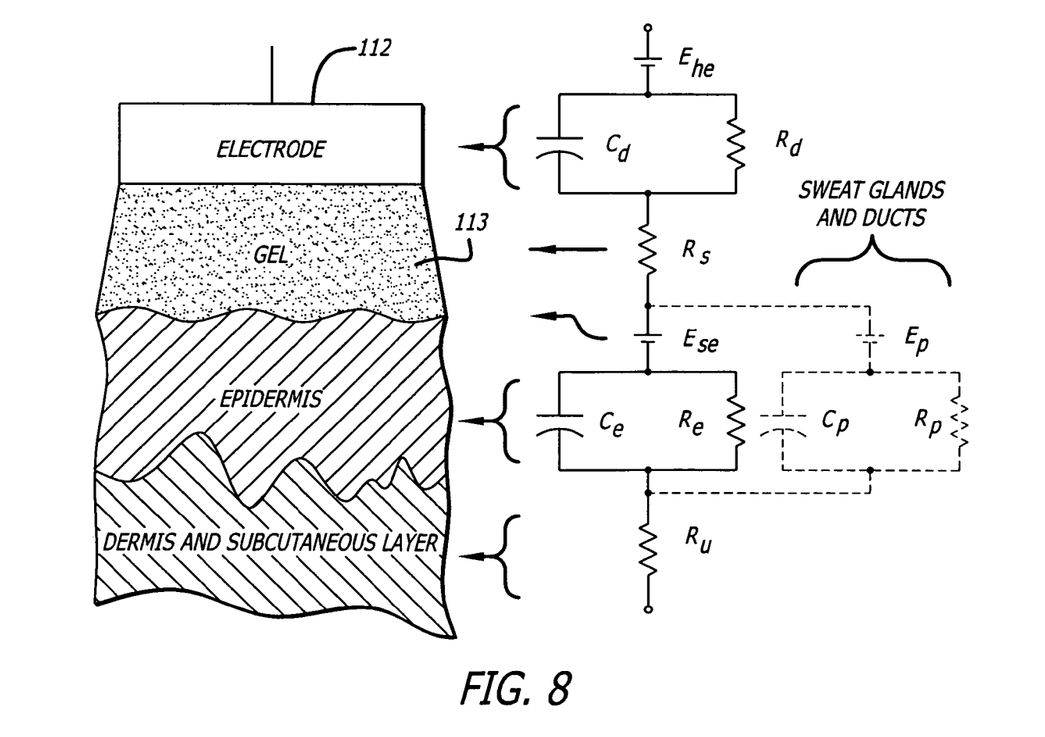
FIG. 8 is a simplified elevational view of an electrode, a patient's skin (on a simplified basis) and a gel for facilitating the coupling between the electrode and the patient's skin and also shows the impedance network formed by the electrode, the gel and the patient's skin.

Each of the layers in FIG. 7 has an impedance. This is shown on a schematic basis in FIG. 8, which shows an electrode, a gel, the epidermis layer and a combination of the dermis and subcutaneous layers. In FIG. 8, the gel is shown as being disposed between the electrode and the epidermis to facilitate the coupling of the electrode to the epidermis layer with a minimal impedance.

Figure 5:
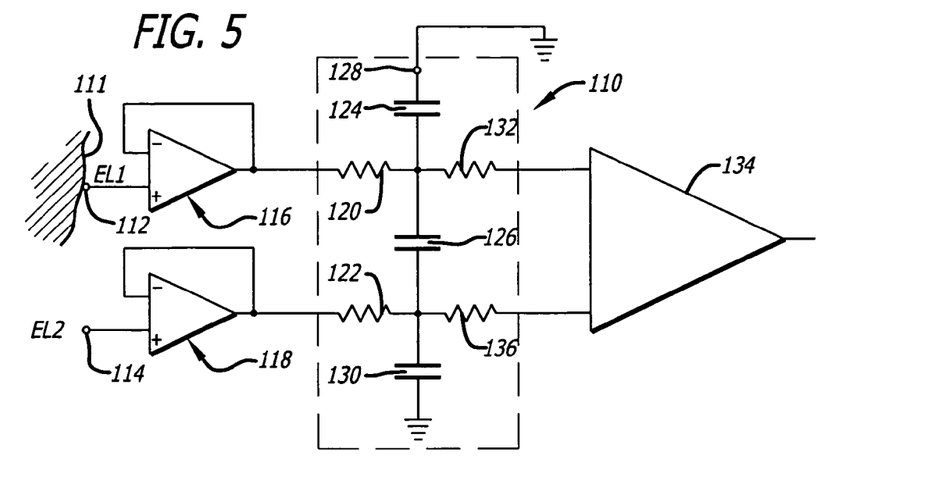
FIG. 5 is a circuit diagram, substantially in block form, of an amplifier system, including a pair of amplifiers and a pair of electrodes, for amplifying low-amplitude signals produced by the patient's heart without affecting the characteristics of the signal and without introducing noise into the signal.

FIG. 5 is a schematic view showing the attachment of an electrode 112 in FIG. 5 to a patient's skin 111 to provide signals for introduction to the amplifier system also shown in FIG. 5. A gel 113 in FIG. 8 may be disposed between the electrode 112 and the patient's epidermis layer to facilitate the attachment of the electrode to the patient's epidermis layer and to reduce impedance. Since each of the layers in the patient's skin has an impedance, the collective impedance of the patient's skin is progressively reduced when the successive layers are removed. With all of the layers in place in the patient's skin, the impedance of the patient's skin may be in the order of several kilohms to megohms. However, the amplifier system in FIG. 5 is constructed to operate satisfactorily even when successive layers are not removed from the patient's skin 111 and the electrode 112 is attached to the epidermis layer.

FIG. 5 is a circuit diagram, primarily in block form, of an amplifier system, generally indicated at 110, constituting a preferred embodiment of the invention disclosed an claimed in application Ser. No. 10/611,696. The amplifier system 110 includes a pair of electrodes 112 and 114 each of which is suitably attached to the patient's skin at a selective position on the patient's body. The electrodes 112 and 114 preferably have an identical construction. The electrode 112 is positioned at a selective position on the skin of the patient's body to produce signals related to the functioning characteristics of an organ in the patient's body. The organ may illustratively be the patient's heart, brain, stomach or intestines. The electrode 114 is positioned on the skin of the patient's body at a position displaced from the selective position to provide reference signals. The difference between the signals at the electrodes 112 and 114 represents the functioning characteristics of the selected one of the patient's organs such as the patient's heart.

The signals on the electrode 112 are introduced to an input terminal of an amplifier generally indicated at 116. The amplifier 116 also has a second input terminal which is connected to the output of the amplifier. In this way, the amplifier acts as a unity gain. The amplifier 116 may be purchased as an OPA 129 amplifier from the Burr-Brown Company which is now a part of Texas Instruments. In like manner, the signals from the electrode 114 are introduced to an input terminal of an amplifier, generally indicated at 118, which may be identical to the amplifier 116. The amplifier 118 has an input terminal which is connected to the output terminal of the amplifier to have the amplifier act as a unity gain.

Resistors 120 and 122 respectively extend from the output terminals of the amplifiers 116 and 118. The resistor 120 is connected to first terminals of capacitors 124 and 126. The second terminal of the capacitor 124 receives a reference potential such as ground. A connection is made from the resistor 122 to the second terminal of the capacitor 126 and to a first terminal of a capacitor 130, the second terminal of which is provided with the reference potential such as ground. The resistors 120 and 122 may have equal values and the capacitors 124 and 130 may also have equal values.

One terminal of a resistor 132 is connected to the terminal common to the capacitors 124 and 126. The other terminal of the resistor 132 has a common connection with a first input terminal of an amplifier 134. In like manner, a resistor 136 having a value equal to that of the resistor 132 is connected at one end to the terminal common to the capacitors 126 and 130 and at the other end to a second input terminal of the amplifier 134.

Since the amplifiers 116 and 118 have identical constructions, they operate to provide signals which represent the difference between the signals on the electrodes 112 and 114. This indicates the functioning of the patient's organ which is being determined by the amplifier system 110. Although the electrodes 112 and 114 are displaced from each other on the skin of the patient's body, they tend to receive the same noise signals. As a result, the difference between the signals on the output terminals of the amplifiers 116 and 118 does not include any noise.

The electrodes 112 and 114 respectively provide an impedance of approximately $10^6$ ohms to the amplifiers 116 and 118. Each of the amplifiers 16 and 18 respectively provides an input impedance of approximately $10^{15}$ ohms. This impedance is so large that it may be considered to approach infinity. This causes each of the amplifiers 116 and 118 to operate as if it has an open circuit at its input. The output impedance of each of the amplifiers 116 and 118 is approximately 50 ohms to 75 ohms.

Because of the effective open circuit at the input of each of the amplifiers 116 and 118, the output signal from each of the amplifiers 116 and 118 corresponds to the input signal to the amplifiers and does not have any less magnitude compared to the amplitude of the input signal to the amplifier. This is important in view of the production of signals in the microvolt or millivolt region in the electrodes 112 and 114.

The capacitors 124, 126 and 130 and the resistors 120 and 122 provide a low-pass filter and a differential circuit and operate to eliminate the noise on the electrodes 112 and 114. The capacitors 124, 126 and 130 also operate to provide signals which eliminate the commonality between the signals in the electrodes 112 and 114 so that only the signals individual to the functionality being determined relative to the selected organ in the patient's body remain. The capacitors 124, 126 and 130 operate as a low pass filter and pass signals in a range to approximately one kilohertz (1 KHz). The signals having a frequency above approximately one kilohertz (1 KHz) are attenuated.

The amplifiers 116 and 118 are identical. Because of this, a description of the construction and operation of the amplifier 116 will apply equally as well to the amplifier 118. The amplifier 116 is shown in detail in FIG. 6. It is manufactured and sold by Burr-Brown in Phoenix, Ariz. and is designated by Burr-Brown as the OPA 129 amplifier.

Figure 6:
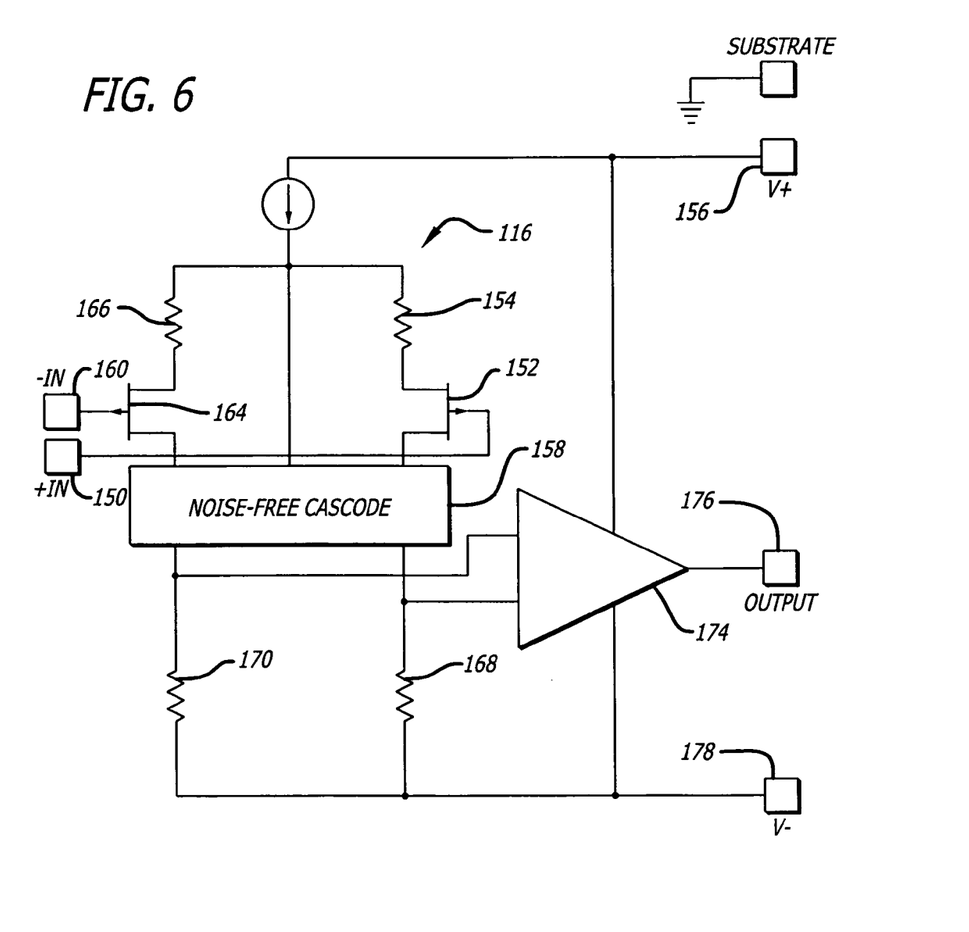
FIG. 6 is a circuit diagram in additional detail of each of the amplifiers included in the amplifier system shown in FIG. 5.

As shown in FIG. 6, the amplifier 116 includes an input terminal 150 which receives the signals at the electrode 112 and introduces these signals to the gate of a transistor 152. The source of the transistor 152 receives a positive voltage from a terminal 156 through a resistor 154. The emitter of the transistor 152 is common with an input terminal in a noise free cascode 158.

Another terminal 160 receives the signals on the electrode 114 and introduces these signals to a gate of a transistor 164. A connection is made from the source of the transistor 164 to one terminal of a resistor 166, the other terminal of which receives the voltage from the terminal 156. The emitter of the transistor 164 is common with an input terminal in the noise-free cascode 158. The resistor 166 has a value equal to that of the resistor 154 and the transistors 152 and 164 have identical characteristics.

First terminals of resistors 168 and 170 having equal values are respectively connected to output terminals in the noise-free cascode 158 and input terminals of an amplifier 174. The amplifier 74 provides an output at a terminal 176. The output from the terminal 176 is introduced to the input terminal 160. The amplifier 174 receives the positive voltage on the terminal 156 and a negative voltage on a terminal 178. Connections are made to the terminal 178 from the second terminals of the resistors 168 and 170.

The transistors 152 and 164 operate on a differential basis to provide an input impedance of approximately $10^{15}$ ohms between the gates of the transistors. The output impedance from the amplifier 116 is approximately fifty (50) ohms to seventy-five (75) ohms. Because of the high input impedance of approximately $10^{15}$ ohms, the amplifier 116 provides an input impedance approaching infinity. This causes the amplifier 116 to provide the equivalent of an open circuit at its input. This causes substantially all of the voltage applied to the input terminal 150 to be provided at the output of the amplifier 116. This is facilitated by the low impedance of approximately fifty ohms (50 ohms) to seventy-five (75) ohms at the output of the amplifier 116. This voltage has characteristics corresponding to the characteristics of the voltage at the electrode 112.

The output signals from the amplifiers 116 and 118 are respectively introduced to the terminal common to the capacitors 124 and 126 and to the terminal common to the capacitors 126 and 130. The capacitors 124, 126 and 130 operate as a low-pass filter to remove noise and to provide an output signal representing the difference between the signals on the electrodes 112 and 114.

The capacitors 124, 126 and 130 correspond to the capacitors C2, C1 and C3 in a low pass filter 176 in application Ser. No. 10/293,105 filed on Nov. 13, 2002 in the USPTO and assigned of record to the assignee of record in this application. The capacitors C2, C1 and C3 in application Ser. No. 10/293,105 are included in the low pass filter 76 in FIG. 8-1 (also shown in FIG. 4) of such application. The low pass filter 76 eliminates noise and passes signals through a frequency range to approximately one kilohertz (1 KHz). If any further information may be needed concerning the construction and operation of the low pass filter, reference may be made to co-pending application Ser. No. 10/293,105 to obtain this information.

Although this invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

I claim:

1. In a method of determining characteristics of a patient's heart, the steps of:
providing signals indicating atypical characteristics of a patient's present heartbeats,
providing signals indicating atypical characteristics of previous heartbeats of the patient,
comparing characteristics of the patient's present and previous atypical heartbeats to select one of the patient's previous atypical heartbeats closest in characteristics to the characteristics of the patient's present atypical heartbeats,
providing atypical heartbeats of third parties, each of the atypical heartbeats of the third parties identifying an individual atypical heart problem different from heart problems identified by other atypical heartbeats of the third parties, and
comparing the selected one of the patient's previous atypical heartbeats and the atypical heartbeats of the third parties to select an individual one of the atypical heartbeats of the third parties closest in characteristics to the characteristics of the selected one of the patient's previous atypical heartbeats and to identify the individual heart problems of the patient; and
diagnosing heart problems of the patient on the basis of the results of the comparison.

2. In a method as set forth in claim 1, the step of:
selecting a course of action dependent upon the characteristics of the selected one of the heartbeats of the third parties.

3. In a method as set forth in claim 2, the step of:
dependent upon the characteristics of the selected one of the atypical heartbeats of the third parties, submitting the selected one of the atypical heartbeats to (a) a doctor for analysis of the selected one of the atypical heartbeats of the third parties, (b) a hospital for analysis of the selected one of the atypical heartbeats of the third parties and (c) an emergency organization for emergency action on the patient.

4. In a method as set forth in claim 1 wherein
each atypical heartbeat includes a plurality of signal portions separated from one another in time and wherein
the signal portions are analyzed from the standpoint of their amplitudes, waveforms, time durations and time separations from one another to determine the characteristics of the atypical heartbeats.

5. In a method as set forth in claim 3 wherein
dependent upon the characteristics of the signal portions of the selected one of the atypical heartbeats of the third parties, submitting the selected one of the atypical heartbeats on a wireless basis to one of (a) a doctor for analysis of the signal portions of the selected one of the atypical heartbeats, (b) a hospital for analysis of the signal portions of the selected one of the atypical heartbeats and (c) an emergency organization for emergency action on the patient.

6. In a method as set forth in claim 3 wherein
each atypical heartbeat includes a plurality of signal portions separated from one another in time and wherein
the signal portions of the selected ones of the atypical heartbeats of the third parties are analyzed from the standpoint of their amplitudes, waveforms, time durations and time separations from one another to determine the characteristics of the atypical heartbeats and wherein
the atypical signals indicating the heartbeat of the patient are obtained from atypical signals of the patient different from a sequence of typical signals of the patient.

7. In a method of determining characteristics of a patient's heart, the steps of:
providing signals having characteristics indicating atypical heartbeats of the patient,
providing signals indicating different types of atypical heartbeats of third parties where the signals individually have characteristics indicating heartbeats from hearts of third parties with different types of atypical heart problems, and comparing the signals indicating the characteristics of the atypical heartbeats of the patient and the signals having characteristics indicating the different types of the atypical heartbeats of the third parties to determine the heart problems of the patient.

8. In a method as set forth in claim 7, the step of:

submitting the determinations of the atypical heart problems of the patient to an individual one of a doctor, a hospital and emergency care dependent upon the severity of the atypical heart problems of the patient.

9. In a method as set forth in claim 8 wherein each atypical heartbeat includes a plurality of signal portions separated from one another in time and wherein the signal portions are analyzed from the standpoint of their amplitudes, waveforms, time durations and time separations from one another to determine the characteristics of the atypical heartbeats.

10. In a method as set forth in claim 7 wherein the signals having characteristics indicating the atypical heartbeats of the patient are obtained by selecting previous atypical heartbeats of the patient for comparison with the signals having characteristics indicating atypical heartbeats of third parties.

11. In a method as set forth in claim 8 wherein the signals indicating previous atypical heartbeats of the patient are stored, and wherein the signals indicating present atypical heartbeats of the patient are compared with the patient's stored atypical heartbeats to select the patient's stored atypical heartbeats closest in characteristics to the characteristics of the patient's present atypical heartbeats, and wherein the signals indicating the atypical heartbeats of the patient are obtained by comparing the selected previous atypical heartbeats of the patient with the signals having characteristics indicating the atypical heartbeats of the third parties.

12. In a method as set forth in claim 7, the steps of:

disposing a heart monitor on an ambulatory patient to obtain the production of said signals having characteristics indicating atypical heartbeats of the patient, amplifying the atypical heartbeat signals of the patient without the production of noise and without changes in the characteristics of the atypical heartbeat signals, providing a server displaced from the patient, transmitting the amplified atypical heartbeat signals of the patient to the server, providing a database of said atypical heartbeat signals of third parties, providing a comparison of the amplified atypical heartbeat signals from the patient and the atypical heartbeat signals from the database to select from the database atypical heartbeat signals having characteristics most closely matching the characteristics of the atypical heartbeat signals from the patient, and transmitting the selected ones of the atypical heartbeat signals from the database to a displaced position, dependent upon the characteristics of the atypical heartbeat signals selected from the database, to obtain an analysis of the patient's heart problems represented by the characteristics of the selected atypical heartbeat signals from the database.

13. In a method as set forth in claim 12 wherein the amplification of the atypical heartbeat signals of the patient is provided by an amplifier with an input impedance approaching infinity and with a low output impedance.

14. In a method as set forth in claim 12 wherein the transmission of the heartbeat signals of the patient to the server is provided by a Bluetooth stage and by a personal digital assistant (PDA).

15. In a method as set forth in claim 12 wherein the atypical signals indicating the heartbeat of the patient are obtained from atypical signals of the patient different from a sequence of typical signals of the patient.

16. In a method as set forth in claim 12 wherein the atypical heartbeat signals have successive signal portions with positive and negative amplitudes and with particular time durations and particular waveforms and wherein determinations are made of the areas and time durations of the successive signal portions in the atypical heartbeat signals of the patient and wherein the determinations of the atypical heartbeat signals of the patient are compared with the determinations of the atypical heartbeat signals at the database to select the database atypical heartbeat signals having characteristics closely matching the characteristics of the atypical heartbeat signals of the patient.

17. In a method as set forth in claim 7, the steps of:

applying a heart monitor to an ambulatory patient to obtain the production of said signals having characteristics indicating atypical heartbeats of the patient, amplifying the atypical heartbeat signals of the patient without generating noise and without affecting the characteristics of the atypical heartbeat signals of the patient, transmitting the amplified atypical heartbeat signals of the patient to a position displaced from the patient, and determining at the displaced position the characteristics of the amplified atypical heartbeat signals of the patient from the standpoint of identifying problems in the patient's heart.

18. In a method as set forth in claim 17 wherein the characteristics of the amplified atypical heartbeat signals from the patient are compared with the characteristics of said atypical heartbeat signals of third parties to determine the heart problems of the patient.

19. In a method as set forth in claim 17 wherein a communication is provided to individual ones of a plurality of medical personnel dependent upon the problems in the patient's heart where the medical personnel include (a) a doctor, (b) a hospital and (c) emergency care.

20. In a method as set forth in claim 18 wherein the atypical heartbeat signals of the third parties being compared with the amplified atypical heartbeat signals of the patient are obtained from a database containing atypical heartbeat signals from third parties with individual and recognized heart problems.

21. In a method as set forth in claim 19 wherein the atypical heartbeat signals of the patient are stored and wherein the stored atypical heartbeat signals of the patient are compared with the atypical heartbeat signals of third parties.

22. In a method as set forth in claim 18 wherein a database is provided of said atypical heartbeat signals of third parties and wherein the amplified atypical heartbeat signals are compared with the atypical heartbeat signals in the database to select an individual one of the atypical heartbeat signals in the database with characteristics close to the characteristics of the individual atypical heartbeat signals of the patient, and a communication is provided to individual ones of a plurality of medical personnel dependent upon the problems in the patient's heart and including (a) a doctor, (b) a hospital and (c) emergency care.

23. In a method as set forth in claim 7, the steps of:

applying a heart monitor to an ambulatory patient to obtain the production of signals indicating the heartbeat of the patient, selecting heartbeat signals of the patient with atypical characteristics, amplifying the selected atypical heartbeat signals of the patient to provide amplified atypical heartbeat signals with the characteristics of the selected atypical heartbeat signals of the patient and without the generation of noise signals, providing a database containing said atypical heartbeat signals of third parties, and comparing the amplified atypical heartbeat signals of the patient with the atypical heartbeat signals from the database to obtain an individual one of the database atypical heartbeat signals with characteristics closest to the characteristics of the selected atypical heartbeat signals of the patient.

24. In a method as set forth in claim 23, the steps of:

providing a processing station which includes atypical heartbeat signals previously generated by the patient, comparing the characteristics of the patient's selected atypical heartbeat signals with the characteristics of the patient's atypical heartbeat signals from the processing station to select, from the processing station, signals closest in characteristics to the characteristics of the selected atypical heartbeat signals of the patient, providing a database of said atypical heartbeat signals of third parties and comparing the characteristics of the atypical heartbeat signals selected from the processing station and provided from the database to obtain an individual one of the database atypical heartbeat signals closest in characteristics to the characteristics of the selected heartbeat signals from the processing station.

25. In a method as set forth in claim 24, the step of:

depending upon the seriousness of the patient's heart problems indicated by the selected database atypical heartbeat signals, communicating the selected database atypical heartbeat signal on a wireless basis to an individual one of the patient's doctor, the patient's hospital and emergency care.

26. In a method as set forth in claim 23 wherein the atypical heartbeat signals from the patient and from the database have successive portions, each having a polarity opposite to the polarity of the adjacent portions and each having an individual time duration and an individual wave shape and an individual peak amplitude and wherein a comparison is made of the polarity, time duration, peak amplitude and wave shape characteristics between the portions in the selected atypical heartbeat signals of the patient and the corresponding portions in the database atypical heartbeat signals to obtain characteristics of the database atypical heartbeat signals closest in characteristics to the selected atypical heartbeat signals of the patient.

27. In a method as set forth in claim 24 wherein the atypical heartbeat signals from the patient and the database have successive portions each having a polarity opposite to the polarity of the adjacent portions and each having an individual time duration and an individual wave shape and an individual peak amplitude and wherein a comparison is made of the polarity, time duration, peak amplitude and wave shape characteristics between the portions in the selected atypical heartbeat signals of the patient and the corresponding portions in the database atypical heartbeat signals to obtain the individual one of the database atypical heartbeat signals closest in characteristics to the characteristics of the selected atypical heartbeat signals of the patient, and wherein dependent upon the seriousness of the patient's heart problems, indicated by the individual one of the selected heartbeat signals, communicating the individual one of the patient's selected heartbeat signals on a wireless basis to an individual one of the patient's doctor, the patient's hospital and emergency care.

28. In a method as set forth in claim 25 wherein the atypical heartbeat signals from the processing station and the database have successive portions each having a polarity opposite to the polarity of the adjacent portions and each having an individual time duration, an individual wave shape and an individual peak amplitude and wherein the heart problems of each individual one of the atypical heartbeat signals in the database are individual and are identified, and wherein a comparison is made of the polarity, time duration, peak amplitude and wave shape characteristics between the portions in the selected atypical heartbeat signals of the patient and the corresponding portions in the processing station to obtain the signals in the processing station closest in characteristics to the characteristics of the selected atypical heartbeat signals in the patient and wherein a comparison is made of the polarity, time duration, peak amplitude and wave shape characteristics between the portions in the database and the corresponding portions in the processing station closest in characteristics to the characteristics of the selected atypical heartbeat signals in the database to obtain the atypical database heartbeat signals closest in characteristics to the characteristics of the selected atypical heartbeat signals in the processing station.

29. In a method set forth in claim 24 wherein the heart problems of each individual one of the atypical heartbeat signals in the database are individual and are identified, and wherein the atypical heartbeat signals from the patient and the database have successive portions, each having a polarity opposite to the polarity of the adjacent portions and each having an individual time duration and an individual wave shape and an individual peak amplitude and wherein a comparison is made of the polarity, time duration, peak amplitude and wave shape characteristics between the portions in each individual one of the selected atypical heartbeat signals of the patient and the corresponding portions in each individual one of the database atypical heartbeat signals to obtain an individual one of the database atypical heartbeat signals closest in characteristics to the characteristics of the selected atypical heartbeat signals of the patient, and wherein the individual one of the database atypical heartbeat signals are transmitted on a wireless basis to an individual one of a doctor, a hospital and emergency care.

30. In combination for determining characteristics of a patient's heart, a monitor constructed to be applied to the patient's heart to produce atypical signals representing characteristics of the patient's heart, an amplifier operatively coupled to the monitor to amplify the atypical signals from the monitor without introducing noise to the signals and without changing the characteristics of the signals from the monitor, a processing station for providing atypical signals previously provided by the patient to represent characteristics of the patient's heart, a pattern recognition platform responsive to the amplified atypical signals and the signals from the processing station for selecting atypical signals from the processing station closest in characteristics to the characteristics of the amplified atypical signals, and electrical circuitry for determining the heart problems of the patient from the atypical signals selected from the processing station, wherein a database provides atypical signals from third parties, the atypical signals having characteristics identifying different types of heart problems in the third parties and wherein a comparator compares the characteristics of the atypical signals selected from the pattern recognition platform and the atypical signals from the database and selects the atypical signals from the database with characteristics closest to the characteristics of the atypical signals selected from the pattern recognition platform.

31. In a combination as set forth in claim 30 wherein the amplifier provides typical signals having characteristics corresponding to signals normally provided by the patient with a normal heart and atypical signals different from the typical signals and representing problems in the patient's heart and wherein the atypical signals from the amplifier are transmitted to the processing station for comparison with the atypical signals from the processing station to select, from the processing station, the atypical signals having characteristics closest to the characteristics of the atypical signals from the amplifier.

32. In a combination as set forth in claim 31 wherein the atypical signals of the patient are stored.

33. In a combination as set forth in claim 30 wherein a detector is operative upon the atypical signals selected from the database to determine the severity of the heart problems of the patient and wherein a transmitter transmits the selected atypical signals to one of a plurality of third parties dependent upon the severity of the heart problems of the patient, each of the third parties indicating the heat problems of the patient for an individual severity.

34. In combination for determining characteristics of a patient's heart, a monitor constructed to be applied to the patient's heart to produce atypical signals representing characteristics of the patient's heart, an amplifier operatively coupled to the monitor to amplify the atypical signals from the monitor without introducing noise to the signals and without changing the characteristics of the signals from the monitor, a processing station for providing atypical signals previously provided by the patient to represent characteristics of the patient's heart, a pattern recognition platform responsive to the amplified atypical signals and the signals from the processing station for selecting atypical signals from the processing station closest in characteristics to the characteristics of the amplified atypical signals, and electrical circuitry for determining the heart problems of the patient from the atypical signals selected from the processing station, wherein a personal digital assistant is responsive to the amplified atypical signals to transmit the amplified atypical signals to server and wherein the amplifier provides typical signals having characteristics corresponding to signals provided by the patient with a normal heart and atypical signals different from the typical signals when the patient has a problem heart and wherein the atypical signals are transmitted to the server for comparison with the signals from the processing station to select, from the processing station the atypical signals having characteristics closest to the characteristics of the atypical signals from the amplifier and wherein the atypical signals from the personal digital assistant are stored and wherein a detector is operative upon the signals selected from the database to determine the severity of the heart problems of the patient and wherein a transmitter transmits the selected atypical signals to one of a plurality of third parties, dependent upon the severity of the heart problems of the patient, each of the third parties identifying heart problems of the patient for heart problems of an individual severity.

35. In a method of determining characteristics of a patient's heart, the steps of:

providing atypical signals indicating problems of the patient's heart, processing the atypical signals of the patient relative to atypical signals of third parties to determine the severity of the problems of the patient's heart, and transmitting the problem atypical signals of the patient on a wireless basis to an individual one of a doctor, a hospital and an emergency station dependent upon the severity of the heart problems of the patient, wherein the atypical heart signals of the patient are compared with atypical signals provided by a database and indicating heart characteristics of third parties where each of the atypical signals in the database identifies an individual type of heart problem different from the heart problems identified by the other atypical signals in the database and wherein the database signals closest in characteristics to the atypical signals of the patient are selected for analysis.

36. In a method as set forth in claim 35 wherein the transmitted signals are atypical from the signals normally provided by the patient when the patient has a normal heart.

37. In a method of determining characteristics of a patient's heart, the steps of:

providing atypical signals indicating problems of the patient's heart, processing the atypical signals of the patient relative to atypical signals of third parties to determine the severity of the problems of the patient's heart, and transmitting the problem atypical signals of the patient to an individual one of a plurality of medical personnel, dependent upon the severity of the heart problems in the patient's heart and including (a) a doctor, (b) a hospital and (c) emergency care, wherein the atypical signals of the patient are compared with atypical signals provided from a pattern recognition platform and constituting atypical signals previously provided by the patient and wherein the atypical signals having characteristics closest in the pattern recognition platform to the characteristics of the atypical signals of the patient are selected for comparison with the atypical heartbeat signals on a database holding atypical heart signals of third parties, each of the heartbeat signals in the database identifying an individual one of a plurality of heart problems.

* * * * *